(12) United States Patent
Keohane et al.

(10) Patent No.: US 11,783,948 B2
(45) Date of Patent: Oct. 10, 2023

(54) COGNITIVE EVALUATION DETERMINED FROM SOCIAL INTERACTIONS

(71) Applicant: INTERNATIONAL BUSINESS MACHINES CORPORATION, Armonk, NY (US)

(72) Inventors: Susann M. Keohane, Austin, TX (US); Nicola Palmarini, Boston, MA (US); Khwaja Jawahar Jahangir Shaik, Jacksonville, FL (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 162 days.

(21) Appl. No.: 16/222,289

(22) Filed: Dec. 17, 2018

(65) Prior Publication Data
US 2020/0194123 A1 Jun. 18, 2020

(51) Int. Cl.
*G16H 50/30* (2018.01)
*G16H 50/50* (2018.01)
(Continued)

(52) U.S. Cl.
CPC ............. *G16H 50/30* (2018.01); *G06Q 50/01* (2013.01); *G08B 21/02* (2013.01); *G16H 50/50* (2018.01)

(58) Field of Classification Search
CPC ........ G16H 50/30; G16H 50/50; G06Q 50/01; G06Q 50/22–24; G06Q 50/20–26; G08B 21/02
(Continued)

(56) References Cited

U.S. PATENT DOCUMENTS 6,334,778 B1 * 1/2002 Brown ................. A61B 5/6896
434/258
8,494,507 B1 * 7/2013 Tedesco ............... G09B 21/009
455/418

(Continued)

OTHER PUBLICATIONS

Kaufman, Lori. (2017). "How to Disable Notification Sounds in Windows 10." (Accessed from Feb. 6, 2017 from Wayback Archive). Retrieved on Jun. 23, 2020 from https://web.archive.org/web/20170206203809/http://www.howtogeek.com/219703/how-to-disable-notification-sounds-in-windows-10/.*

(Continued)

*Primary Examiner* — Jason S Tiedeman
*Assistant Examiner* — Jessica Marie Webb
(74) *Attorney, Agent, or Firm* — Tutunjian & Bitetto, P.C.; Stosch Sabo (57) ABSTRACT

A computer-implemented method, system, and computer program product are provided for determining cognitive issues. The method includes building, by a processor device with social network data, a patient model for social interactions between a patient and other people. The method also includes computing, by the processor device, changes between the patient model and new social network data. The method additionally includes evaluating, by the processor device, the changes between the patient model and new social network data to generate evaluated changes. The method further includes determining, by the processor device, a patient metric score responsive the evaluated changes. The method also includes controlling an operation of a processor-controlled device responsive to the patient metric score.

20 Claims, 8 Drawing Sheets

(51) Int. Cl.
  *G06Q 50/10* (2012.01)
  *G08B 21/02* (2006.01)
  *G06Q 50/00* (2012.01)
(58) Field of Classification Search
  USPC .......................................................... 705/2, 3
  See application file for complete search history.

(56) References Cited

U.S. PATENT DOCUMENTS

| | | | |
|---|---|---|---|
| 9,308,446 | B1 | 4/2016 | Merzenich et al. |
| 9,474,481 | B2 | 10/2016 | Dagum |
| 9,787,941 | B1* | 10/2017 | Brooksby ............... G10L 15/26 |
| 9,836,581 | B2* | 12/2017 | Madan ................... G16H 50/30 |
| 9,849,364 | B2* | 12/2017 | Tran ......................... A61B 5/11 |
| 2008/0015904 | A1* | 1/2008 | Lubell ..................... G16H 10/65 |
| | | | 705/3 |
| 2010/0049095 | A1* | 2/2010 | Bunn ...................... G16H 40/60 |
| | | | 600/595 |
| 2012/0232430 | A1* | 9/2012 | Boissy ................... A61B 5/1118 |
| | | | 600/595 |
| 2013/0212638 | A1* | 8/2013 | Wilson ................... G06Q 50/26 |
| | | | 726/1 |
| 2013/0253283 | A1* | 9/2013 | Hudson ................ A61B 5/4058 |
| | | | 600/300 |
| 2014/0041047 | A1* | 2/2014 | Jaye ..................... G06F 21/6263 |
| | | | 726/27 |
| 2014/0377727 | A1* | 12/2014 | Yom-Tov .............. G06F 16/951 |
| | | | 434/236 |
| 2015/0081299 | A1 | 3/2015 | Jasinschi et al. |
| 2015/0213207 | A1* | 7/2015 | Amarasingham ...... G16H 40/20 |
| | | | 705/2 |
| 2015/0216413 | A1* | 8/2015 | Soyao .................... G16H 20/60 |
| | | | 709/204 |
| 2017/0004260 | A1* | 1/2017 | Moturu .................. G16H 50/20 |
| 2017/0169191 | A1* | 6/2017 | Bowers .................. G16H 15/00 |
| 2017/0172462 | A1* | 6/2017 | Alghazi ................... A45B 3/00 |
| 2017/0177814 | A1* | 6/2017 | Abedini ................. G16H 50/20 |
| 2018/0090024 | A1 | 3/2018 | Somers et al. |
| 2018/0196882 | A1* | 7/2018 | Abou Mahmoud ........................ |
| | | | G06F 16/9535 |
| 2018/0360370 | A1* | 12/2018 | Hamilton, II ........ A61B 5/4088 |
| 2019/0080055 | A1* | 3/2019 | Bettencourt Da Silva .................. |
| | | | G16H 40/63 |
| 2019/0172157 | A1* | 6/2019 | Keohane ................ G06V 40/10 |
| 2020/0066397 | A1* | 2/2020 | Rai ....................... G06Q 10/067 |
| 2020/0075165 | A1* | 3/2020 | Lieberman ............. G16H 30/40 |
| 2020/0129780 | A1* | 4/2020 | Lachaine ............... G16H 50/50 |

OTHER PUBLICATIONS

J. Kim, S. Kwon, S. Seo and K. Park, "Highly wearable galvanic skin response sensor using flexible and conductive polymer foam," 2014 36th Annual International Conference of the IEEE Engineering in Medicine and Biology Society, Chicago, IL, 2014, pp. 6631-6634, doi: 10.1109/EMBC.2014.6945148.*
N.a.) Combine and merge files into one PDF. Oct. 28, 2017. Adobe. all pages. Accessed via Wayback Archive: https://web.archive.org/web/20171028234437/https://acrobat.adobe.com/us/en/acrobat/how-to/merge-combine-pdf-files-online.html (Year: 2017).*
Model. (2015). In The Editors of the American Heritage Dictionaries (Ed.), The American Heritage Dictionary of Medicine (2nd ed.). Houghton Miffl in. Credo Reference:https://search.credoreference.com/content/entry/hmmedicaldict/model/0?institutionld=743 (Year: 2015).*
Medical model. (1992). In C. G. Morris (Ed.), Academic Press Dictionary of Science and Technology (4th ed.).Elsevier Science & Technology. Credo Reference:https://search.credoreference.com/content/entry/apdst/medical_model/0?institutionld=743 (Year: 1992).*
Machine learning. (1992). In C. G. Morris (Ed.), Academic Press Dictionary of Science and Technology (4th ed.). Elsevier Science & Technology. Credo Reference:https://search.credoreference.com/content/entry/apdst/machine_learning/0?institutionld=743 (Year: 1992).*
Zhang, Peng. "Architectures and Patterns for Moving towards the Use of High-Frequency, Low-Fidelity Data in Healthcare". Sep. 30, 2018. ProQuest Dissertations Publishing. all pages, esp. Abstract. (Year: 2018).*
Lu, Chenyang. "Diabetes Management System for a New Type 2 Diabetes Geriatric Cohort: Improve the Interaction of Self-management". 2017. ProQuest Dissertations Publishing. all pages. (Year: 2017).*
Anonymous, "Social Data Analysis as Unobtrusive Measure for Validating Human Behavior Assessment of Test (Psychometric) Results", An IP.com Prior Art Database Technical Disclosure, Jun. 2011, 10 pages.
Anonymous, "Cognitive System and Method to Identify Symptoms and Patterns of Possible Harmful Virtual Interaction to the Psychological Integrity of Participants", An IP.com Prior Art Database Technical Disclosure, May 2016, 7 pages.
Anonymous, "Wearable Device for Measuring Social Interactions" An IP com Prior Art Database Technical Disclosure, Jan. 2018, 3 pages.
Anonymous, "Method and System for Cognitively Developing Social Interaction Skills of a User by Correlating Contextual Data of User Emotions", An IP.com Prior Art Database Technical Disclosure May 2018, 3 pages.
Chen, "Understanding the Influence of Social Interactions on Individual's Behavior Pattern in a Work Environment", International Workshop on Human Behavior Understanding, Nov. 2011, pp. 146-157.
"Social and Behavioral Theories", e-Source Behavioral & Social Sciences Research, Aug. 2018, 40 pages.

* cited by examiner

Build, with social network data, a patient model for social interactions between a patient and other people.
810

Generate a thumbprint for the patient and people known to the patient.
812

Utilize the physical characteristics of the patient for identifying the patient in the new social network data.
813

Compute changes between the patient model and new social network data.
820

Evaluate the changes between the patient model and new social network data to generate evaluated changes.
830

Catalog and Classify emotions of the patient in the new social network data when interacting with both known people and unknown people.
832

Develop patterns over time of interactions the patient has with known people.
834

Determine a patient metric score responsive the evaluated changes.
840

Control an operation of a processor-controlled device responsive to the patient metric score.
850

COGNITIVE EVALUATION DETERMINED FROM SOCIAL INTERACTIONS

BACKGROUND

Technical Field

The present invention generally relates to cognitive impairment, and more particularly to determining cognitive issues using social interaction between people.

Description of the Related Art

Cognitive evaluations can be an issue. Identification of cognitive issues can be challenging for family, friends, and medical personal. A challenge during cognitive evaluations is the need to measure social interaction and how the social interactions are measured.

SUMMARY

In accordance with an embodiment of the present invention, a computer-implemented method is provided for determining cognitive issues. The method includes building, by a processor device with social network data, a patient model for social interactions between a patient and other people. The method also includes computing, by the processor device, changes between the patient model and new social network data. The method additionally includes evaluating, by the processor device, the changes between the patient model and new social network data to generate evaluated changes. The method further includes determining, by the processor device, a patient metric score responsive the evaluated changes. The method also includes controlling an operation of a processor-controlled device responsive to the patient metric score.

In accordance with another embodiment of the present invention, a computer program product is provided for determining cognitive issues. The computer program product includes a non-transitory computer readable storage medium having program instructions. The program instructions are executable by a computer to cause the computer to perform a method. The method includes building, by a processor device with social network data, a patient model for social interactions between a patient and other people. The method also includes computing, by the processor device, changes between the patient model and new social network data. The method additionally includes evaluating, by the processor device, the changes between the patient model and new social network data to generate evaluated changes. The method further includes determining, by the processor device, a patient metric score responsive the evaluated changes. The method also includes controlling an operation of a processor-controlled device responsive to the patient metric score.

In accordance with yet another embodiment of the present invention, a cognitive detection system is provided. The cognitive detection system includes a communication system connected to a communication network. The cognitive detection system also includes a processing system having a processor device and memory receiving social network data. The processing system is programmed to build, with the social network data, a patient model for social interactions between a patient and other people. The processing system is also programmed to compute changes between the patient model and new social network data. The processing system is additionally programmed to evaluate the changes between the patient model and new social network data to generate evaluated changes. The processing system is further programmed to determine a patient metric score responsive the evaluated changes. The processing system is also programmed to control an operation of a processor-controlled device responsive to the patient metric score.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein.

DETAILED DESCRIPTION

Embodiments in accordance with the present invention provide methods and apparatuses for determining cognitive issues in people using social interactions. Social interactions between people can be used to identify changes in individuals. Social interaction can be utilized to detect the onset of cognitive impairment or changes in a person's cognitive impairment. Social interactions can include the use of social media feeds, e.g., Facebook®, Instagram®, LinkedIn®, and Twitter®, or personal interactions at a home or a business.

Figure 1:
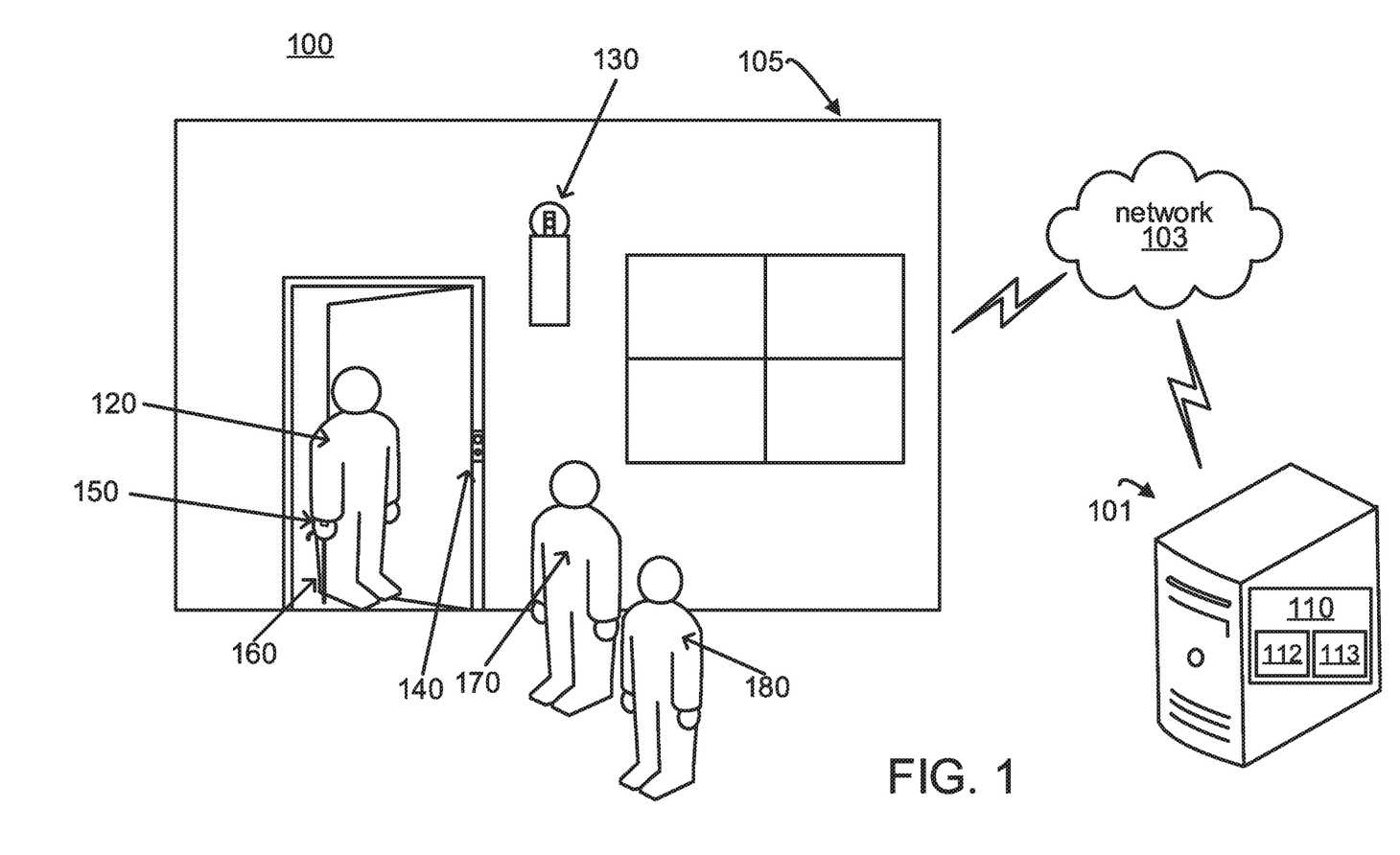
FIG. 1 an exemplary environment to which the present invention can be applied, in accordance with an embodiment of the present invention.

Referring now to the drawings in which like numerals represent the same or similar elements and initially to FIG. 1, an exemplary environment 100 to which the present invention can be applied according to an embodiment of the present invention. A cognitive detection system 110 (CDS) can collect social network data for a patient 120 to both create and train a patient model 112 and to monitor the patient 120 with the patient model 112 for changes over time that can be caused by cognitive issues. The CDS 110 can keep the patient model 112 segregated to only permit authorized personnel access to any one particular patient model 112 for security purposes. The CDS 110 can employ encryption to protect the patient model 112.

The patient model 112 can be composed of an aggregate of available data sources which the individual has given permission to use, e.g., insights from sensors detecting activities of daily living (ADL) and social interactions, driving records, emergency medical services, social media, etc. The patient model 112 for the individual can run machine learning or artificial intelligence techniques to analyze new data collected, e.g., feature extraction, detect and classify normal and abnormal behavior. A characteristic profile of the individual can be built to begin to look at similar cohorts for matching patterns in order to help with early detection of cognitive issues.

The patient model 112 can consist of several inferences from different data streams. Relationships between people and objects and histories of their condition over time can be detected using machine learning for real time anomaly detection. For example, if we use IoT sensor data to track "leaving home" which is a good sign for avoiding isolation then a probabilistic model can be built via observations to map the sensor(s) firing to a behavior event called "leaving the home". A set of sensors(s) can be assigned to the event and capture an aggregate count of each sensor over a period of time (minutes, hours, days, etc.). The probabilistic model can be employed to predict when certain sensors will fire, for how long, at which time on a given hour, day, week and so on. A probability can be assigned for that type of event and thus describe in probabilistic terms what is estimated as "normal" or set a threshold for "abnormal" (e.g., abnormal behavior could be leaving the house at 3 am). Over time, the patient model 112 can be taught to adjust what is considered normal and abnormal. Inferences gathered from different data sources can be employed to begin to correlate behavior events. An example correlation is upcoming doctor appoints in the electronic medical records to sensor firings that map to leaving the house.

The CDS 110 can include a permission engine 113. The permission engine 113 can manage the extent implementations of the invention collect, store, or employ personal information provided by, or obtained from, individuals (for example, current locations of drivers, historical records of drivers, etc.), such information shall be used in accordance with all applicable laws concerning protection of personal information. Additionally, the permission engine 113 can manage the collection, storage, and use of such information that may be subject to consent of the individual, i.e., user, to such activity, for example, through "opt-in" or "opt-out" processes as may be appropriate for the situation and type of information. The permission engine 113 can manage the storage and use of personal information in an appropriately secure manner reflective of the type of information, for example, through various encryption and anonymization techniques for particularly sensitive information.

The permission engine 113 can not only permit the individual to "opt-in" or "opt-out" of the data collection but can also permit the individual to "opt-in" or "opt-out" of the insights derived from the data. For example, the data can provide insights on how many interactions the person has had over a period of time which can provide an insight that the individual is at risk of depression due to isolation/loneliness. The individual could choose to track interactions but withdraw permission to infer his/her mental status (e.g., depression).

The CDS 110 can automatically collect social network data from the patient's social media accounts to build and train the patient model. The social network data can include, e.g., information to determine the patient's relationships with known people 170, physical characteristics of the patient 120 and known people 170 that interact with the patient 120, audio information for determining the patient's voice and the voices of the known people 170, etc. The physical characteristics can include, e.g., height, posture, mass, hair color, complexion, eye color, etc. The CDS 110 can automatically collect information from sensors in a home 105 or a care facility. The sensors can permit the CDS 110 to gather audio data and video data of the patient 120 and the known people 170. The sensors can include detection equipment from a security system, e.g., cameras, infrared sensors, and microphones.

In one embodiment, the sensors can be included in internet of thing (IoT) devices, e.g., a doorbell camera 140, a light with a camera 130, a smart thermostat, a smart refrigerator, a personal assistant device, a smart microwave, etc. The IoT devices can include high-resolution cameras and microphones, low-resolution cameras and microphone, and infrared sensors. In another embodiment, the sensors can be included in wearable device or personal devices, e.g., a smart watch 150, a fitness tracker, a smart cane 160, etc. The wearable device or personal devices can include multiple sensors, e.g., a camera, a microphone, a global positioning system (GPS), an altimeter, a gyroscope, pressure sensors, Wi-Fi, etc. The sensors can monitor the patient 120 and the known people 170 for physical characteristics and for interactions. In one embodiment, the patient 120 can utilize the smart cane 160 that includes a GPS, a gyroscope, and a pressure sensor to monitor the patients 120 location and physical dependence on the smart cane 160. The change of physical dependence on the smart cane 160 can point to an ailment that could change the demeanor of the patient 120, e.g., the patient 120 is not feeling well, leans harder on the smart cane 160, and becomes less social, which can explain a change in social interaction not related to increased cognitive issues. The sensors included in the IoT devices, wearables, and personal devices permit non-intrusive monitoring of the patient 120 and the known people 170.

The sensors can communicate with the CDS 110 over a network 103. The network 103 can be wired or wireless, e.g., a local area network, a wide area network, a cellular network, a Wi-Fi network, etc. In one embodiment, the CDS 110 can be located on-site at the home or care facility. In another embodiment, the CDS 110 can be located at a remote location. The CDS 110 can be a standalone system or integrated into a larger system. The CDS 110 can include can be run from a server 101 or from the cloud.

The CDS 110 can create thumbprints for both the patient 120 and the known people 170 that interact with the patient 120 from the social network data. The CDS 110 can collect other information for both the thumbprint generation and the monitoring of the patient 120. This other information can include infrared signatures of the patient 120 or the known people 170 and gate patterns of the patient 120 or the known people 170 walking or running to identify the patient 120 or the known people 170. The thumbprints can be in the patient model 112 to monitor changes in interactions between the patient 120 and the known people 170. The thumbprints of the patient 120 and the known people 170 can be shared between patient models 112 for different patients 120, e.g., patients 120 or staff at a group care facility. The thumbprints permit the CDS 110 to identify people to monitor changes in interactions between the patient 120 and the known people 170. The CDS 110 can identify unknown people 180 interacting with the patient 120 when no thumbprint for the unknown person 180 is included in the patent model 112. The CDS 110 can permit patients 120 to opt-in or opt-out of the monitoring with the permission engine 113, this can include whether the patient model 112 is generated and whether a thumbprint is generated for an individual. The ability to opt-out can be useful in a shared care facility, e.g., group home, to let patients 120 control whether they want to be monitored and to leave the patients 120 at easy about the collection of social network data.

Figure 2:
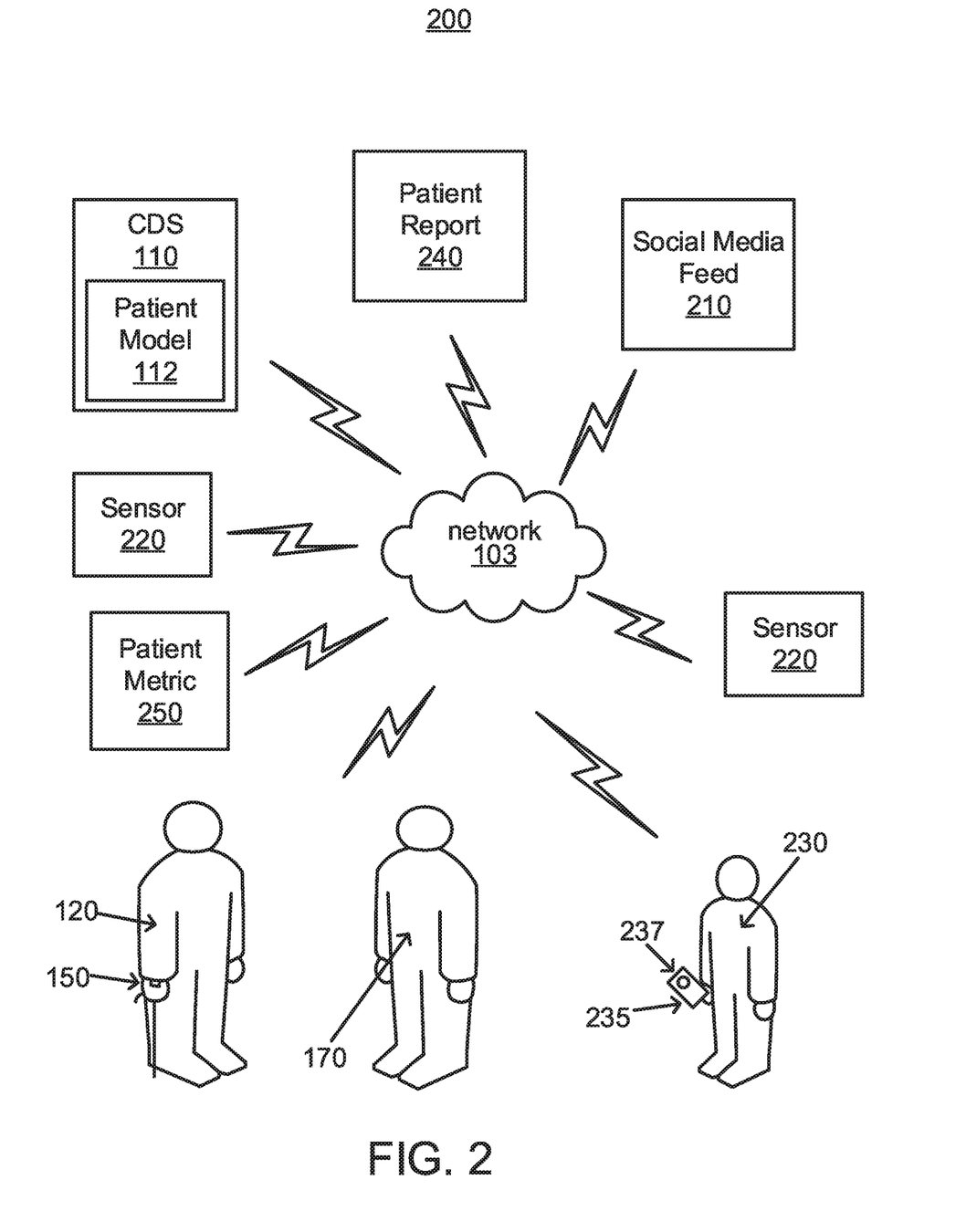
FIG. 2 is a block/flow diagram of an exemplary environment to which the present invention can be applied, in accordance with an embodiment of the present invention.

FIG. 2 is a block/flow diagram of an exemplary environment 200 to which the present invention can be applied, in accordance with an embodiment of the present invention. The CDS 110 can include the patient model 112 that can be created and trained from social network data from the patient 120. The CDS 110 can gather more social network data from the patient 120. The CDS 110 can continue to monitor sensors 220 near the patient 120 and a social media feed 210 of the patient 120 to determine if the cognitive state of the patient 120 has changed. The CDS 110 can collect information related to who meets or interacts with the patient 120, e.g., the known people 170. The CDS 110 can correlate who interacts with the patient 120 with multiple criteria, e.g., when the interaction occurs, what are the content and context of the interaction, the emotional and physical sentiment of the patient 120 and the known people 170 during the interaction, e.g., friendly, hostile, benign, etc. The interactions can occur on-line or in person. The in-person interactions can include the patient 120 and both the known people 170 and the unknown people 180.

In one embodiment, the patient 120 and the known people 170 can be interacting in person. The proximity of the patient 120 and the known people 170 can be detected to determine the sentiment of the patient 120. The proximity can be detected from video data of the interaction. In other examples, the proximity can be detected utilizing Bluetooth® or Wi-Fi from devices on the patient 120 and the known people 170. These devices can also be employed to determine the identity of the known person 170 or the known people 170 can be identified with audio data from the interaction utilizing audio analytics. Additional information can be collected from the interaction, e.g., the interaction duration, the speed of replies by the patient 120, the level of engagement or interest by the patient 120.

In another embodiment, the patient 120 can wear the smart watch 150 that can analyze the patient 120 using the smart watch 150 by skin contact during an interaction with the known people 170. This analysis can include the health parameters, e.g., blood pressure, heart rate, etc. The mood, emotion state, and stress levels of the patient 120 can be determined from the smart watch 150 using technologies in sweat analysis. The interaction information can be analyzed to classify the in-person interaction to detect changes in behavior or cognitive state in the patient 120. The CDS 110 can employ this information to develop patterns of regular activity for the patient 120, e.g., frequency of interactions, duration of interactions, time of day of the interactions, day of the week of interactions, etc. For example, the patient 120 normally interacts with the known people 170, e.g., a dog walker or a maid, on Wednesdays. The learned patterns of the patient 120 can be employed by the CDS 110 to alert a caregiver 230 to a change in patterns, e.g., outliers of the pattern, etc. The caregiver 230 can be alerted by an electronic message 237 or through an application on a mobile device, e.g., a mobile phone 235, a tablet, a laptop, etc. In another embodiment, the caregiver 230 can be alerted with an audible alarm, e.g., when in a group care facility or hospital. In one example, the patient 120 normally interacts with the known people 170, e.g., a maid, on Wednesdays, but now they are interacting on Thursday and Friday of a week. The CDS 110 can send an alert, e.g., an electronic message 237, to the caregiver 230, so the caregiver 230 can check on the patient 120 to ensure the patient 120 is safe and the known people 170 is not taking advantage of the patient 120, e.g., getting paid multiple times in a week for the same work.

The CDS 110 can utilize the patient model 112 with current interaction information to predict future interactions between the patient 120 and the known people 170. In one embodiment, the CDS 110 can predict that the known person 170, e.g., the maid, will be interacting with the patient 120 on Wednesdays at the home 105. This prediction can be utilized by the caregiver 230 to be on site to directly observe the interaction between the patient 120 and the known person 170. The CDS 110 can correlate the interactions of the patient 120 with the health status of the patient 120. This correlation can include positive interactions with the known people 170 and the unknown people 180. The correlation can also include negative interactions with the known people 170 and the unknown people 180. The CDS 110 can determine if the patient 120 may be affected by loneliness behavior, which can have negative health consequences.

The CDS 110 can utilize the patient model 112 and the interactions of the patient 120 to generate a patient report 240. The patient report 240 can be generated and sent to the caregiver 230. The patient report 240 can also be sent to medical personnel for further analysis. The patient report 240 can include both generic and detailed information regarding the patient 120 and the interactions the patient 120 has with both the known people 170 and the unknown people 180. For example, the patient report 240 can include, e.g., a daily summary of the known people 170 and the unknown people 180 interacting with the patient 120, a number of people around the patient 120 at certain times or on certain days, a daily summary of interactions of the patient 120, the length of the interactions the patient 120 had with the known people 170 and the unknown people 180, the location of the interaction, the time of day of the interaction, the tone or sentiment of the interaction, the mood of the patient 120 during the interaction, a log of interactions the patient 120 has over different time periods, e.g., hourly, mornings, evenings, a given day of the week, a week, a month, a season, a year, etc.

The CDS 110 can generate a patient metric 250 responsive to the interactions of the patient 120. Changes in the patient metric 250 can point to cognitive issues, e.g., the patient metric 250 decreases. For example, night time wandering can be an early indicator of cognitive issues or dementia. Abnormal pacing or movement patterns in the house, forgetting to turn off burners, oven or other appliances, lack of grooming (e.g., showering) can also be indicators of cognitive issues. Each activity has associated data that can be collected to provide evidence and run thru machine learning or artificial intelligence techniques to detect what's considered normal or abnormal for the patient 120. There can also be a "new" normal or new baseline as time goes progresses.

The patient metric 250 can be utilized to encourage behavioral modification of the patient 120, the CDS 110 can incentivize the patient 120 to be more socially active. The patient metric 250 can be responsive to, e.g., the number of interactions, the type of interactions, the length of interactions, the content of the interactions, etc. Changes in the patient metric 250 can be utilized to reward the patient 120. The patient metric 250 can be employed by multiple patients to compare the patient 120 progress in this area. The patient metric 250 can be utilized to create a community of the patients 120 that want to improve their social interactions or health of safety reasons. The patient metric 250 can be employed to win rewards, e.g., the IBM® health care vitality application.

Figure 3:
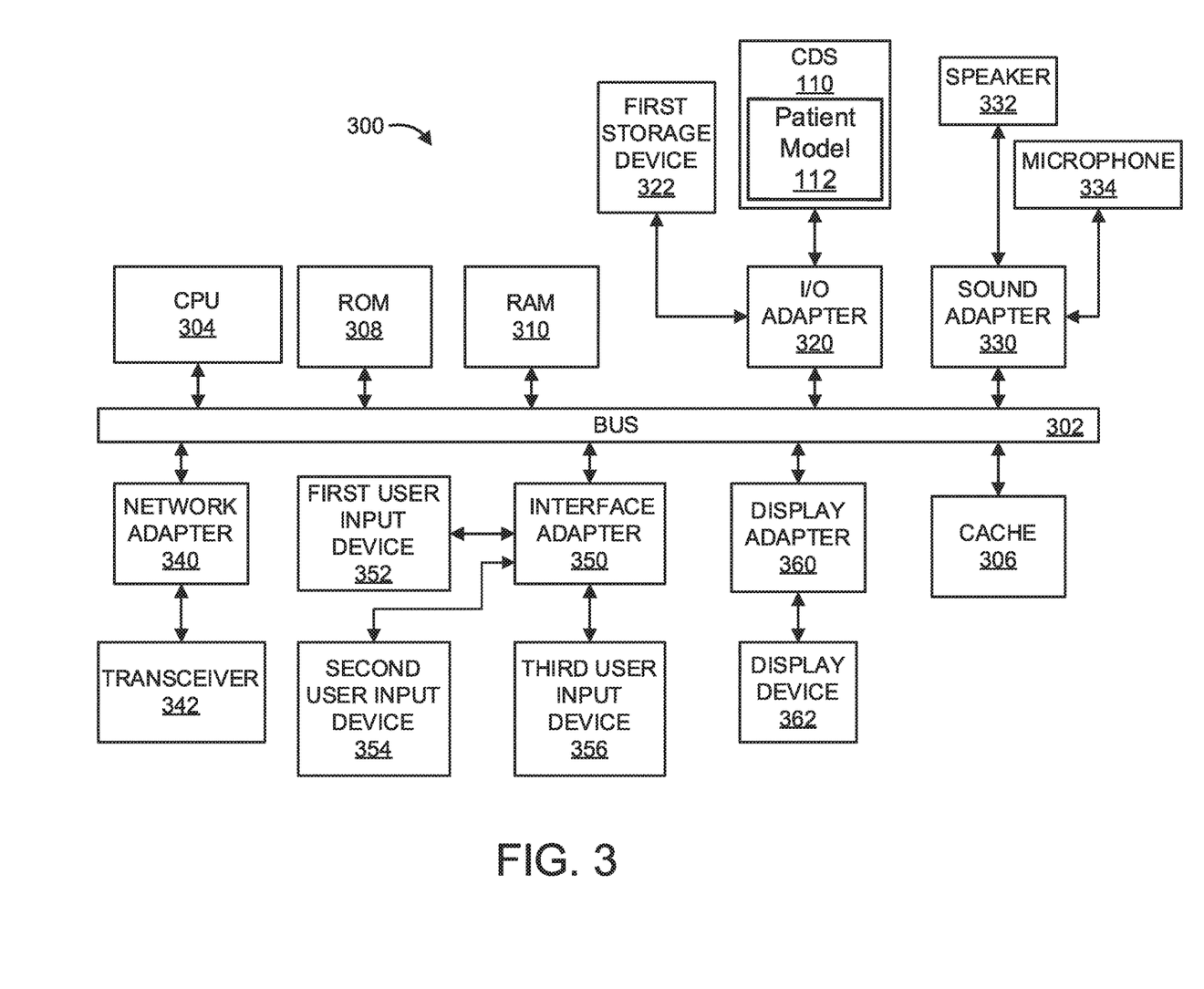
FIG. 3 is a block/flow diagram of an exemplary processing system with a cognitive detection system, in accordance with embodiments of the present invention.

FIG. 3 is an exemplary processing system 300 with a CDS 110, in accordance with an embodiment of the present invention. The processing system 300 includes at least one processor (CPU) 304 operatively coupled to other components via a system bus 302. A cache 306, a Read Only Memory (ROM) 308, a Random Access Memory (RAM) 310, an input/output (I/O) adapter 320, a sound adapter 330, a network adapter 340, a user interface adapter 350, and a display adapter 360, are operatively coupled to the system bus 302.

A first storage device 322 is operatively coupled to system bus 302 by the I/O adapter 320. The storage device 322 can be any of a disk storage device (e.g., a magnetic or optical disk storage device), a solid state magnetic device, and so forth. The CDS 110 can be coupled to the system bus 302 by the I/O adapter 320. The CDS 110 can receive audio and video data with the processing system 300. The CDS 110 can include the patient model 112 that can be trained with the received audio and video data.

A speaker 332 and a microphone 334 are operatively coupled to system bus 302 by the sound adapter 330. A transceiver 342 is operatively coupled to system bus 302 by network adapter 340. A display device 362 is operatively coupled to system bus 302 by display adapter 360.

A first user input device 352, a second user input device 354, and a third user input device 356 are operatively coupled to system bus 302 by user interface adapter 350. The user input devices 352, 354, and 356 can be any of a keyboard, a mouse, a keypad, an image capture device, a motion sensing device, a microphone, a device incorporating the functionality of at least two of the preceding devices, and so forth. Of course, other types of input devices can also be used in embodiments of the present invention. The user input devices 352, 354, and 356 can be the same type of user input device or different types of user input devices. The user input devices 352, 354, and 356 are used to input and output information to and from system 300.

Of course, the processing system 300 may also include other elements (not shown), as readily contemplated by one of skill in the art, as well as omit certain elements. For example, various other input devices and/or output devices can be included in processing system 300, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the processing system 300 are readily contemplated by one of ordinary skill in the art given the teachings of the present invention provided herein.

Moreover, it is to be appreciated that environment 100 described above with respect to FIG. 1 is an environment for implementing respective embodiments of the present invention. Part or all of processing system 300 may be implemented in one or more of the elements of environment 100.

Further, it is to be appreciated that processing system 300 may perform at least part of the method described herein including, for example, at least part of the CDS 110 of FIG. 1 and/or at least part of the CDS 110 of FIG. 2.

Figure 4:
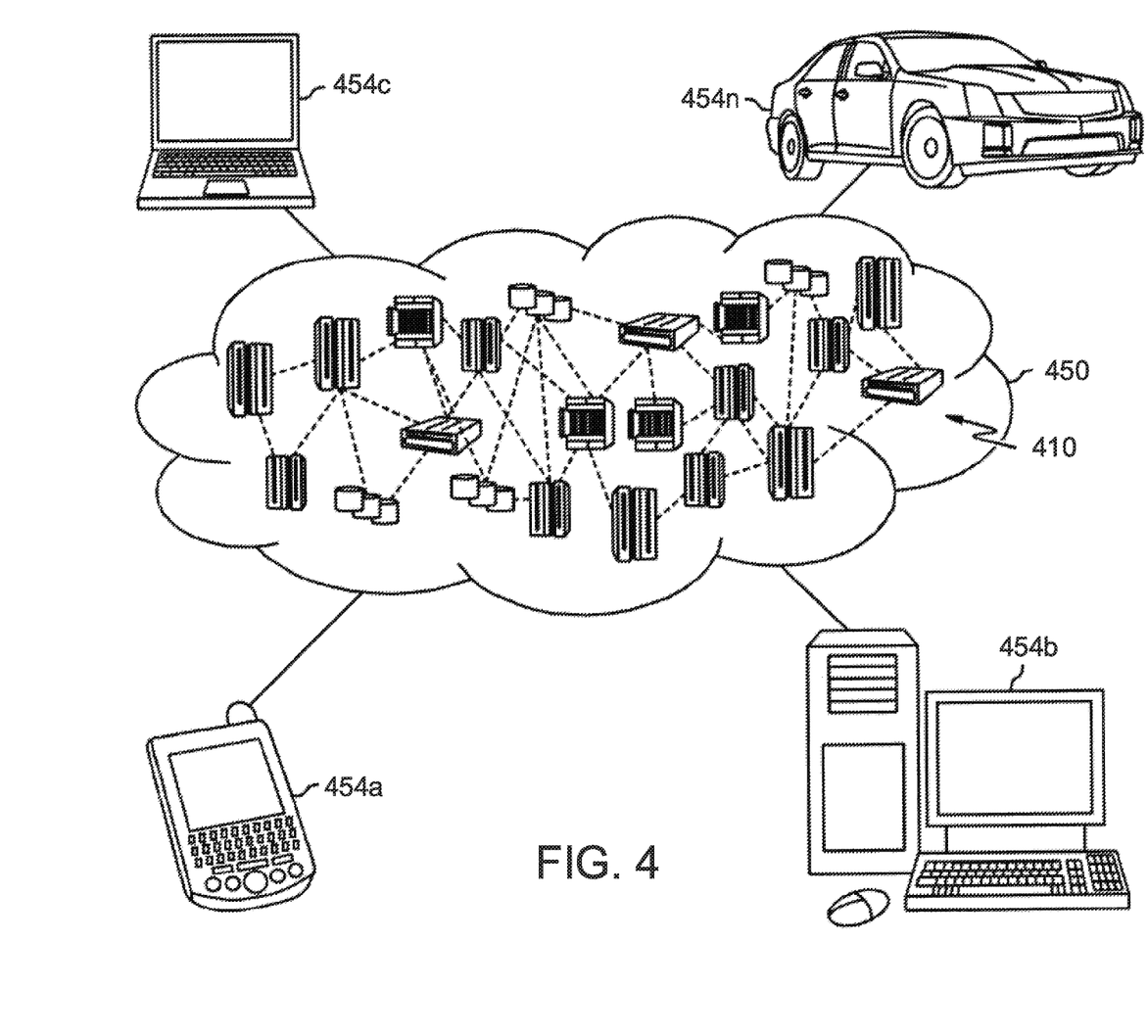
FIG. 4 is a block/flow diagram of an exemplary cloud computing environment, in accordance with an embodiment of the present invention.

FIG. 4 is a block/flow diagram of an exemplary cloud computing environment, in accordance with an embodiment of the present invention.

It is to be understood that although this invention includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model can include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but can be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It can be managed by the organization or a third party and can exist on-premises or off-premises.

Community cloud: the cloud infrastructure is shared by several organizations and supports a specific community that has shared concerns (e.g., mission, security requirements, policy, and compliance considerations). It can be managed by the organizations or a third party and can exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 4, illustrative cloud computing environment 450 is depicted for enabling use cases of the present invention. As shown, cloud computing environment 450 includes one or more cloud computing nodes 410 with which local computing devices used by cloud consumers, such as, for example, personal digital assistant (PDA) or cellular telephone 454A, desktop computer 454B, laptop computer 454C, and/or automobile computer system 454N can communicate. Nodes 410 can communicate with one another. They can be grouped (not shown) physically or virtually, in one or more networks, such as Private, Community, Public, or Hybrid clouds as described hereinabove, or a combination thereof. This allows cloud computing environment 450 to offer infrastructure, platforms and/or software as services for which a cloud consumer does not need to maintain resources on a local computing device. It is understood that the types of computing devices 454A-N shown in FIG. 4 are intended to be illustrative only and that computing nodes 410 and cloud computing environment 450 can communicate with any type of computerized device over any type of network and/or network addressable connection (e.g., using a web browser).

Figure 5:
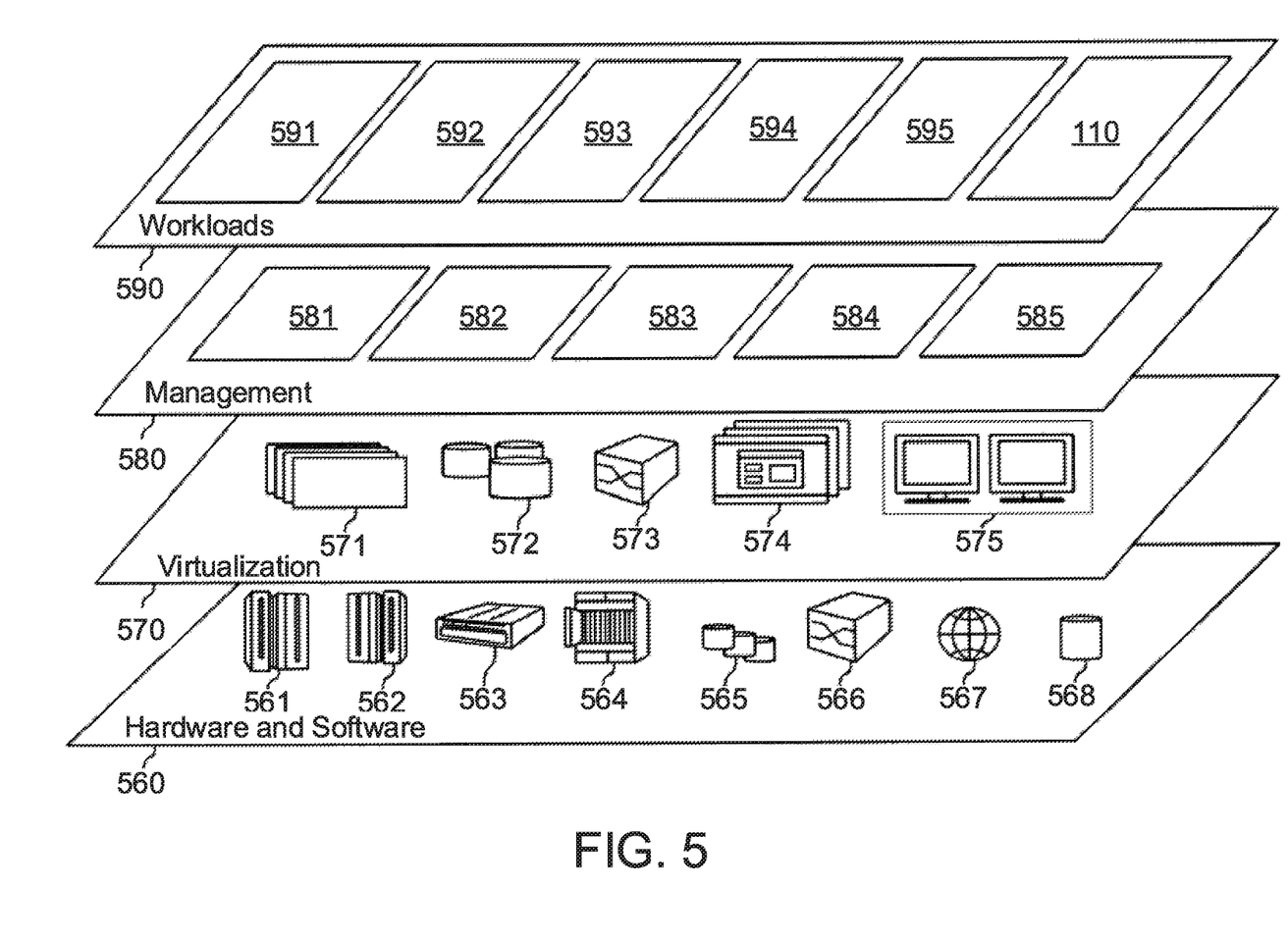
FIG. 5 is a schematic diagram of exemplary abstraction model layers, in accordance with an embodiment of the present invention.

FIG. 5 is a schematic diagram of exemplary abstraction model layers, in accordance with an embodiment of the present invention. It should be understood in advance that the components, layers, and functions shown in FIG. 5 are intended to be illustrative only and embodiments of the invention are not limited thereto. As depicted, the following layers and corresponding functions are provided:

Hardware and software layer 560 includes hardware and software components. Examples of hardware components include: mainframes 561; RISC (Reduced Instruction Set Computer) architecture based servers 562; servers 563; blade servers 564; storage devices 565; and networks and networking components 566. In some embodiments, software components include network application server software 567 and database software 568.

Virtualization layer 570 provides an abstraction layer from which the following examples of virtual entities can be provided: virtual servers 571; virtual storage 572; virtual networks 573, including virtual private networks; virtual applications and operating systems 574; and virtual clients 575.

In one example, management layer 580 can provide the functions described below.

Resource provisioning 581 provides dynamic procurement of computing resources and other resources that are utilized to perform tasks within the cloud computing environment. Metering and Pricing 582 provide cost tracking as resources are utilized within the cloud computing environment, and billing or invoicing for consumption of these resources. In one example, these resources can include application software licenses. Security provides identity verification for cloud consumers and tasks, as well as protection for data and other resources. User portal 583 provides access to the cloud computing environment for consumers and system administrators. Service level management 584 provides cloud computing resource allocation and management such that required service levels are met. Service Level Agreement (SLA) planning and fulfillment 585 provide pre-arrangement for, and procurement of, cloud computing resources for which a future requirement is anticipated in accordance with an SLA.

Workloads layer 590 provides examples of functionality for which the cloud computing environment can be utilized. Examples of workloads and functions which can be provided from this layer include: mapping and navigation 591; software development and lifecycle management 592; virtual classroom education delivery 593; data analytics processing 594; transaction processing 595; and the CDS 110.

Figure 6:
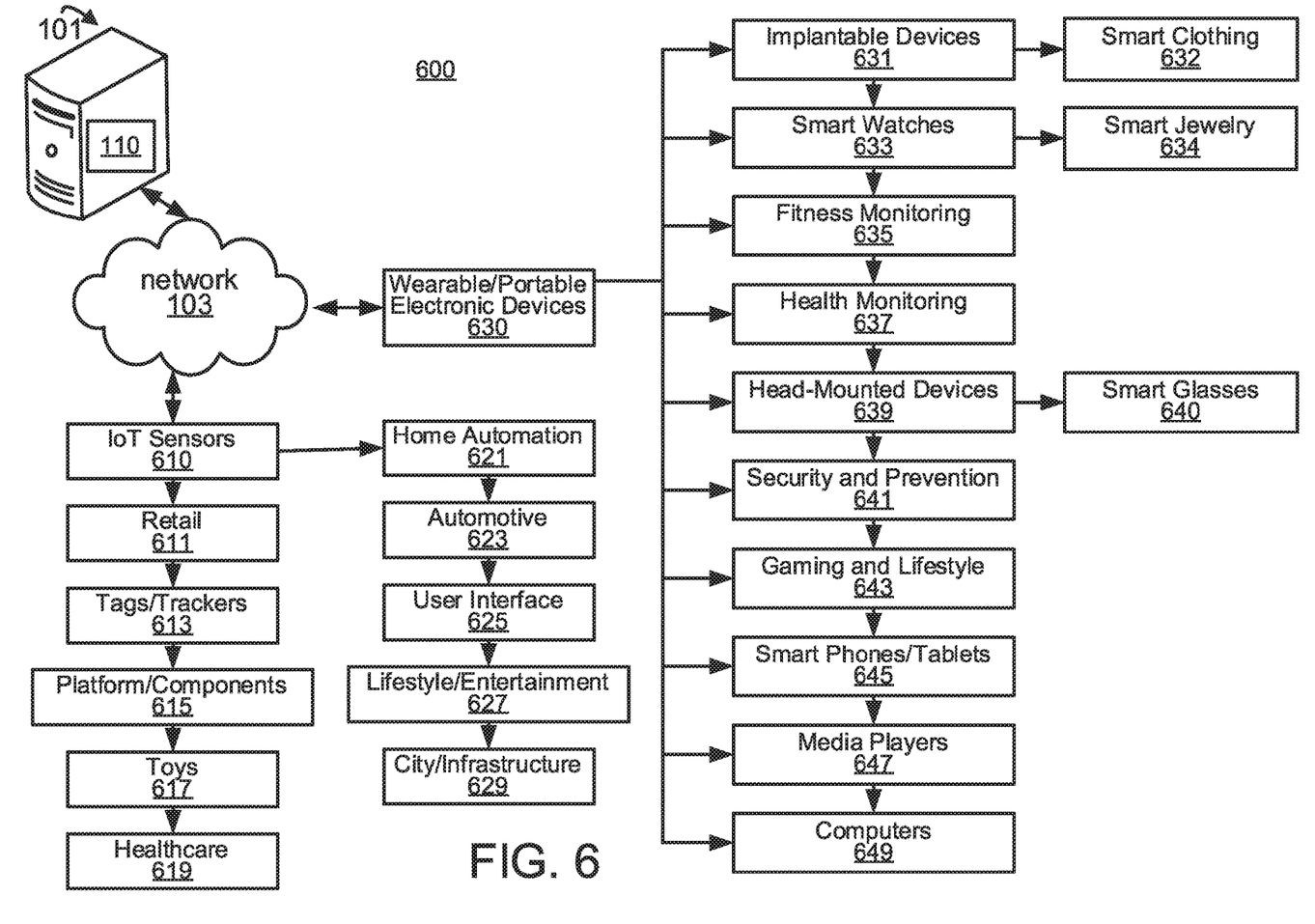
FIG. 6 is a block diagram of an exemplary environment to which the present invention can be applied, in accordance with embodiments of the present invention.

FIG. 6 shows an exemplary environment 600 to which the present invention can be applied, in accordance with an embodiment of the present invention.

IoT is an advanced automation and analytics system which exploits networking, sensing, big data, and artificial intelligence technology to deliver complete systems for a product or service. These systems allow greater transparency, control, and performance when applied to any industry or system. IoT systems have applications across industries through their unique flexibility and ability to be suitable in any environment. They enhance data collection, automation, operations, and much more through smart devices and powerful enabling technology. IoT systems allow users to achieve deeper automation, analysis, and integration within a system. They improve the reach of these areas and their accuracy. IoT utilizes existing and emerging technology for sensing, networking, and robotics. Features of IoT include artificial intelligence, connectivity, sensors, active engagement, and small device use.

In various embodiments, the CDS 110 can receive IoT data, e.g., audio, video, or other data, from the IoT systems. The IoT data can be received by a computer processing system 101 via a network 103. For example, the computer processing systems 101 can receive the IoT data from wearable or portable electronic devices 630. Wearable/portable electronic devices 630 can include implantable devices 631, such as smart clothing 632. Wearable/portable devices 630 can include, e.g., smart watches 633, as well as smart jewelry 634. Wearable/portable devices 630 can further include fitness monitoring devices 635, health and wellness monitoring devices 637, head-mounted devices 639 (e.g., smart glasses 640), security and prevention systems 641, gaming and lifestyle devices 643, smart phones/tablets 645, media players 647, and/or computers/computing devices 649.

The computer processing systems 101 can also receive the IoT data from sensors 610 for various applications, such as home automation 621, automotive 623, user interface 625, lifestyle and/or entertainment 627, city and/or infrastructure 629, retail 611, tags and/or trackers 613, platform and components 615, toys 617, and/or healthcare 619. The IoT sensors 610 can communicate with the computer processing systems 101 via network 103. Of course, one skilled in the art can contemplate using the computer processing systems 101 to receive IoT data for other types of applications, not limited to the ones described herein.

Figure 7:
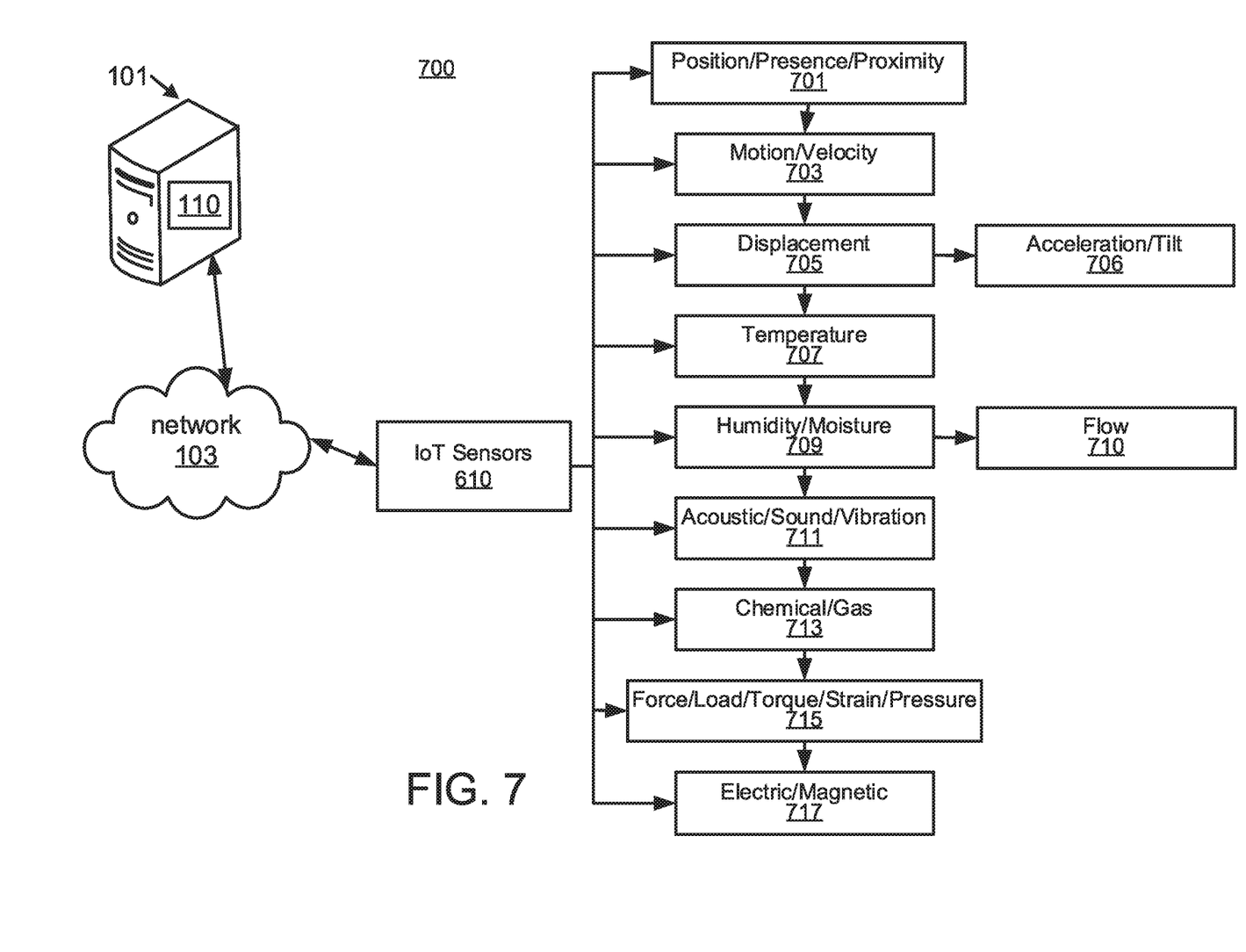
FIG. 7 is block diagram of an exemplary environment to which the present invention can be applied, in accordance with embodiments of the present invention.

FIG. 7 shows an exemplary environment 700 to which the present invention can be applied, in accordance with an embodiment of the present invention.

IoT loses its distinction without sensors. IoT sensors act as defining instruments which transform IoT from a standard passive network of devices into an active system capable of real-world integration.

The IoT sensors 610 can be connected via network 103 to transmit information/data, continuously and in in real-time, to the computer processing systems 101, which includes the CDS 110. Exemplary IoT sensors 610 can include, but are not limited to, position/presence/proximity sensors 701, motion/velocity sensors 703, displacement sensors 705, such as acceleration/tilt sensors 706, temperature sensors 707, humidity/moisture sensors 709, as well as flow sensors 710, acoustic/sound/vibration sensors 711, chemical/gas sensors 713, force/load/torque/strain/pressure sensors 715, and/or electric/magnetic sensors 717. One skilled in the art can contemplate using any combination of such sensors to collect IoT data to be analyzed by the CDS 110. One skilled in the art can contemplate using other types of IoT sensors, such as, but not limited to, magnetometers, gyroscopes, image sensors, light sensors, radio frequency identification (RFID) sensors, and/or micro flow sensors. IoT sensors can also include energy modules, power management modules, RF modules, and sensing modules. RF modules manage communications through their signal processing, Wi-Fi, ZigBee®, Bluetooth®, radio transceiver, duplexer, etc.

Moreover, data collection software can be used to manage sensing, measurements, light data filtering, light data security, and aggregation of data. Data collection software uses certain protocols to aid IoT sensors in connecting with real-time, machine-to-machine networks (e.g., that send IoT data to the CDS 110). Then the data collection software collects data from multiple devices and distributes it in accordance with settings. Data collection software also works in reverse by distributing data over devices. The system can eventually transmit all collected data to, e.g., a central server.

Additionally, real-time analytics applications take data or input from various devices and convert it into viable actions or clear patterns for human analysis. They analyze information based on various settings and designs in order to perform automation-related tasks or provide the data required by industry. In the instant case, real-time analytics applications can aid the current system in sending log messages, analyzing log messages, parsing log messages, and using the heterogenous log pattern editing recommendation system 110, as well as detecting anomalies.

Figure 8:
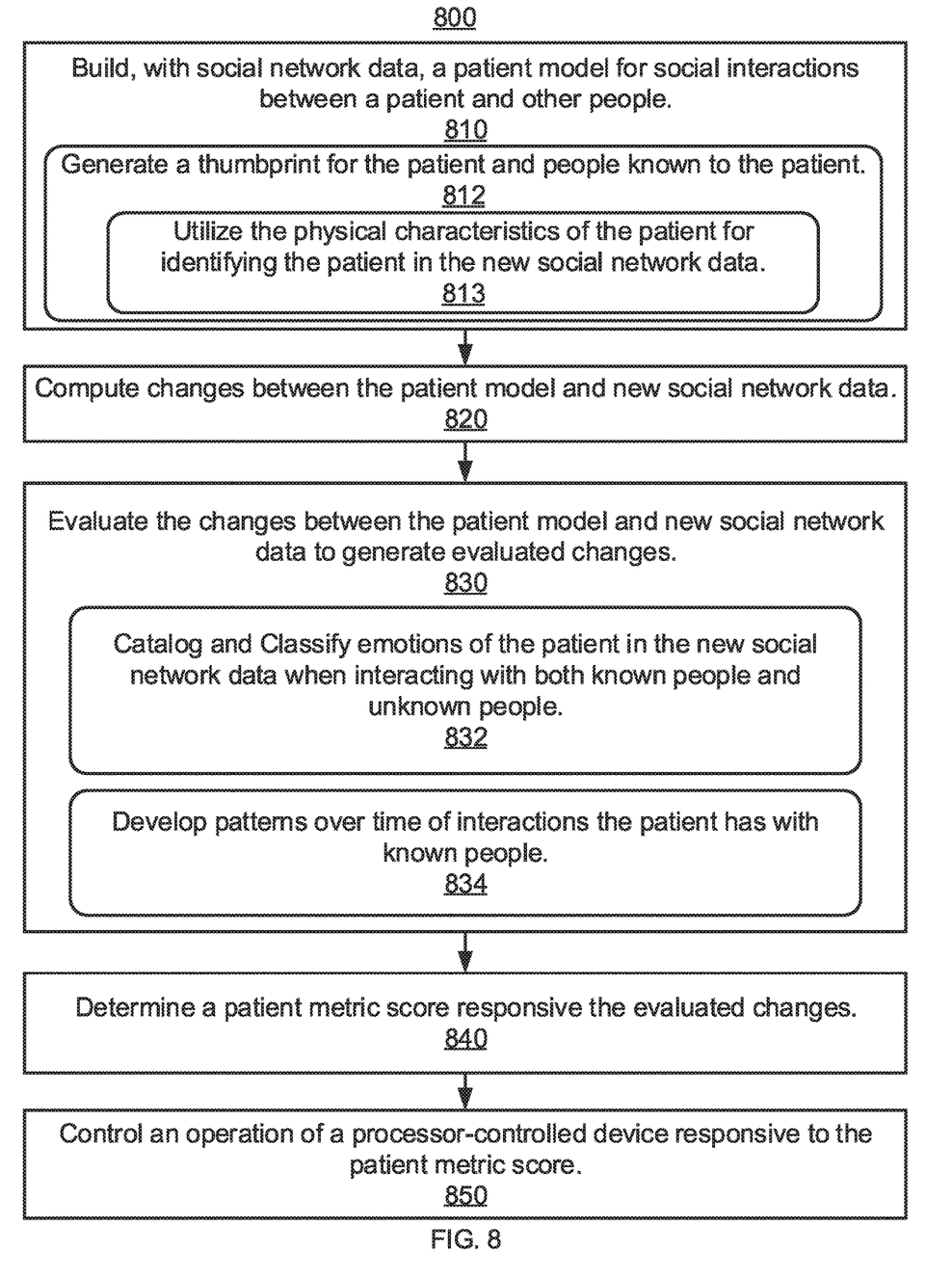
FIG. 8 is a block/flow diagram showing the cognitive issues determination method, in accordance with an embodiment of the present invention.

Referring to FIG. 8, methods for determining cognitive issues are illustratively shown and described. In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In block 810, a patient model is built with social network data showing social interactions between a patient and other people. In block 812, a thumbprint is generated for the patient and people known to the patient. In block 813, the physical characteristics of the patient are utilized for identifying the patient in the new social network data. In block 820, changes are computed between the patient model and new social network data. In block 830, the changes between the patient model and new social network data are evaluated to generate evaluated changes. In block 832, emotions of the patient in the new social network data are cataloged and classified when interacting with both known people and unknown people. In block 834, patterns are developed over time of interactions the patient has with known people. In block 840, a patient metric score is determined responsive the evaluated changes. In block 850, an operation of a processor-controlled device is controlled responsive to the patient metric score.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as SMALLTALK, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Having described preferred embodiments of systems and methods for determining cognitive issues in people using social interactions (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

The invention claimed is:

1. A computer-implemented method for determining cognitive issues, comprising:
   converting, by a processor device, motions detected by body worn acceleration sensors and images captured by cameras of a security system into descriptions forming a patient's information data including social network data and daily living data, both relating to activities of daily living including social interactions, interaction durations, and interaction reply speeds by a patient, the patient's information data further including an emotional sentiment data associated with the social interactions;
   training, by the processor device, a patient machine learning model on the patient's information data to generate a trained patient machine learning model, the trained patient machine learning model outputting a baseline for the patient, the baseline including the social interactions, the interaction durations, the interaction reply speeds, and the emotional sentiment data associated with the social interactions, the baseline being normal behavior and routines for the patient indicated by information data for the patient;
   computing, by the processor device, changes between the baseline for the patient from the output of the trained patient machine learning model and new information data for the patient obtained from the body worn acceleration sensors and the cameras of the security system; and
   evaluating, by the processor device, the changes between the baseline for the patient from the output of the trained patient machine learning model and the new information data for the patient in relation to the baseline to generate an indication as to whether the new information data for the patient is classified as normal or abnormal based on a probabilistic model.

2. The computer-implemented method as recited in claim 1, wherein converting includes receiving social media feeds for the patient.

3. The computer-implemented method as recited in claim 1, wherein converting includes receiving audio data and video data from an area around the patient.

4. The computer-implemented method as recited in claim 1, further comprising generating a thumbprint for the patient and people known to the patient.

5. The computer-implemented method as recited in claim 4, wherein generating the thumbprint includes utilizing physical characteristics of the patient for identifying the patient in the new social network data.

6. The computer-implemented method as recited in claim 1, wherein evaluating includes cataloging and classifying emotions of the patient in the new social network data when interacting with both known people and unknown people.

7. The computer-implemented method as recited in claim 1, further comprising sounding an alarm for a caregiver to intervene when the patient is interacting abnormally.

8. The computer-implemented method as recited in claim 1, wherein evaluating includes developing patterns over time of interactions the patient has with known people.

9. The computer-implemented method as recited in claim 8, wherein the patterns are selected from the group consisting of frequency of interaction, time of day of interaction, and day of week of interaction.

10. The computer-implemented method as recited in claim 1, wherein evaluating includes analyzing sweat from the patient to detect a mood of the patient.

11. The computer-implemented method as recited in claim 1, wherein the new information data for the patient is gathered from internet of things devices.

12. A computer program product for determining cognitive impairment, the computer program product comprising a non-transitory computer readable storage medium having program instructions embodied therewith, the program instructions executable by a computer to cause the computer to perform a method comprising:
   converting, by a processor device, motions detected by body worn acceleration sensors and images captured by cameras of a security system into descriptions forming a patient's information data including social network data and daily living data both relating to activities of daily living including social interactions, interaction durations, and interaction reply speeds by a patient, the patient's information further including an emotional sentiment data associated with the social interactions;
   training, by the processor device, a patient machine learning model on the patient's information data to generate a trained patient machine learning model, the trained patient machine learning model outputting a baseline for the patient, the baseline including the social interactions, the interaction durations, the interaction reply speeds, and the emotional sentiment data associated with the social interactions, the baseline being normal behavior and routines for the patient indicated by information data for the patient;
   computing, by the processor device, changes between the baseline for the patient from the output of the trained patient machine learning model and new information data for the patient obtained from the body worn acceleration sensors and cameras of the security system; and
   evaluating, by the processor device, the changes between the baseline for the patient from the output of the trained patient machine learning model and the new information data for the patient in relation to the baseline to generate an indication as to whether the new information data for the patient is classified as normal or abnormal based on probabilistic model.

13. A cognitive detection system for determining cognitive impairment, comprising:
   a communication system connected to a communication network;
   a processing system including a processor device and memory receiving a patient's information data, the processing system programmed to:
      convert motions detected by body worn acceleration sensors and images captured by cameras of a security system into descriptions forming a patient's information data including social network data and daily living data, both relating to activities of daily living including social interactions, interaction durations, and interaction reply speeds by a patient, the patient's information data further including an emotional sentiment data associated with the social interactions;
      train a patient machine learning model on the patient's information data to generate a trained patient machine learning model, the trained patient model outputting a baseline for the patient, the baseline including the social interactions between the patient and other people, the interaction durations, and the interaction reply speeds by the patient, the baseline being normal behavior and routines of the patient indicated by information data for the patient;

compute changes between the baseline for the patient from the output of the trained patient machine learning model and new information data for the patient obtained from the body worn acceleration sensors and cameras of the security system; and evaluate the changes between the baseline for the patient from the output of the trained patient machine learning model and the new information data for the patient in relation to the baseline to generate an indication as to whether the now information data for the patient is classified as normal or abnormal based on a probabilistic model.

14. The system as recited in claim 13, further comprising a wearable device that can analyze sweat of a wearer to determine mood.

15. The system as recited in claim 13, further programmed to develop patterns over time of interactions the patient has with known people.

16. The system as recited in claim 15, wherein the patterns are selected from the group consisting of frequency of interaction, time of day of interaction, and day of week of interaction.

17. The system as recited in claim 13, further programmed to generate a thumbprint for the patient utilizing physical characteristics of the patient for identifying the patient in the new information data for the patient.

18. The system as cited in claim 13, wherein the patient's information data include social media feeds for the patient.

19. The system as recited in claim 13, further programmed to gather the new information data for the patient from internet of things devices.

20. The computer-implemented method as recited in claim 1, wherein the emotional sentiment of the social interactions is selected from the group consisting of friendly, hostile, and benign.

* * * * *